(12) United States Patent
Moenkemoeller

(10) Patent No.: US 12,151,056 B2
(45) Date of Patent: Nov. 26, 2024

(54) SERVICE COVER FOR FILTER SLOT OF VEHICLE AIR CONDITIONER

(71) Applicant: Ralf Moenkemoeller, Bielefeld (DE)

(72) Inventor: Ralf Moenkemoeller, Bielefeld (DE)

(73) Assignee: HEPA GmbH, Muenster (DE)

(\*) Notice: Subject to any disclaimer, the term of this patent is extended or adjusted under 35 U.S.C. 154(b) by 712 days.

(21) Appl. No.: 17/376,294

(22) Filed: Jul. 15, 2021

(65) Prior Publication Data

US 2023/0014115 A1    Jan. 19, 2023

(30) Foreign Application Priority Data

Jul. 30, 2020    (DE) .................... 102020004626.6

(51) Int. Cl.
| | | |
|---|---|---|
| *A61L 9/22* | (2006.01) |
| *A61L 9/015* | (2006.01) |
| *B60H 1/00* | (2006.01) |
| *B60H 1/22* | (2006.01) |
| *B60H 3/06* | (2006.01) |
| *B60L 1/02* | (2006.01) |
| *B61H 1/00* | (2006.01) |

(52) U.S. Cl.
CPC ............... *A61L 9/22* (2013.01); *A61L 9/015* (2013.01); *B60H 1/00585* (2013.01); *B60H 1/2225* (2013.01); *B60H 3/0616* (2013.01); *B60L 1/02* (2013.01); *A61L 2209/11* (2013.01); *A61L 2209/16* (2013.01)

(58) Field of Classification Search
CPC ........ A61L 9/22; A61L 9/015; A61L 2209/11; A61L 2209/16; B60L 1/02; B60H 3/0616; B60H 1/00585; B60H 1/2225
See application file for complete search history.

(56) References Cited

FOREIGN PATENT DOCUMENTS

WO    WO 2010/128480    *    5/2010

\* cited by examiner

*Primary Examiner* — Lessanework Seifu

(74) *Attorney, Agent, or Firm* — Andrew Wilford

(57) ABSTRACT

In order to guarantee reliable maintenance, a reliable energy supply and simple handling of the service cover and the vehicle air conditioner at the smallest possible structural cost, it is proposed that the service cover has electrical means, by means of which an air-treatment device arranged within the vehicle air conditioner can be supplied with the electrical energy necessary in order to operate said air-treatment device from outside the vehicle air conditioner.

9 Claims, 1 Drawing Sheet

SERVICE COVER FOR FILTER SLOT OF VEHICLE AIR CONDITIONER

FIELD OF THE INVENTION

The invention relates to a service cover for closing the service port of a filter slot in a vehicle air conditioner.

BACKGROUND OF THE INVENTION

Vehicle air conditioners installed in motor vehicles usually have a service cover of this kind that can easily close the filter slot of the vehicle air conditioner and and can also open this filter slot in order to carry out maintenance, replacement and repair work. For example, after the service cover has been opened, a used filter fitted inside the filter slot can be replaced for a fresh filter. After the filter has been replaced, the service cover can then easily be closed again.

Air-treatment units are used in vehicle air conditioners of this kind and these can be installed in the vehicle air conditioner after a filter has been removed through the service port of the filter slot, for example. Air-treatment units of this kind may be designed as ionizer, ozone generator and/or electrical heaters, for example.

Once the air-treatment device has been assembled or fitted, the vehicle air conditioner is closed again by the service cover.

Air-treatment units, for example an ionizer as mentioned above, must be supplied with electrical energy. This must be fed to the air-treatment device from outside the vehicle air conditioner.

OBJECT OF THE INVENTION

Starting from the prior art as described above, the problem addressed by the invention is that of providing a service cover for closing the service port of a filter slot of a vehicle air conditioner for easily achieving the exchange of air-treatment devices installed in the vehicle air conditioner can and for supplying electrical energy to air-treatment devices of this kind in a structurally simple manner.

SUMMARY OF THE INVENTION

This problem is solved according to the invention in that the service cover has electrical means which enable an air-treatment device arranged within the vehicle air conditioner to be supplied with the electrical energy necessary in order to operate this air-treatment device from outside the vehicle air conditioner.

If the service cover has a contact means on the service cover side for connection to a contact or coding means of the air-treatment device, it is possible to detect from the service cover which variant, model or type of air-treatment device is installed in the vehicle air conditioner.

In order to allow simple control with or without feedback of the air-treatment device, it is advantageous for an electrical controller to be configured or arranged in the service cover to provide operating voltage to the air-treatment device, and to connect to the contact or coding means of the air-treatment system where necessary. The air-treatment device can therefore be operated according to the operating parameters provided for the respective variant of the air-treatment device by the controller on the service cover side, which retrieves the electrical contact or coding means from the air-treatment device.

The design variant of the air-treatment device is clearly established by the electrical contact or coding means of this air-treatment device. A wide variety of variants of the air-treatment device can be operated by the controller, which is configured as a universal controller, in accordance with the operating parameters provided for it which are prescribed by the vehicle air conditioner in which the air-treatment device is installed.

In order to guarantee reliable operation of the vehicle air conditioner equipped with the service cover according to the invention, it is advantageous if the electrical controller of the service cover can reduce the operating voltage produced by this controller to values which do not represent a danger to life and/or switched off when the service port of the filter slot of the vehicle air conditioner is open and/or when the electrical connection between the electrical controller, on the one hand, and the coding means of the air-treatment device, on the other, is interrupted.

In order to provide a vehicle air conditioner installed in a motor vehicle with additional functions, it is advantageous for an air treatment device for installation in a vehicle air conditioner of this kind to be designed as a retrofit set and to have an air-treatment device and a service cover, as have been described above.

The electrical contact or coding means is advantageously characteristic of the variant of the air-treatment device, can be brought into electrical connection with the controller during assembly of the air-treatment device and the service cover and after the electrical connection to the controller has been made, data can be retrieved therefrom.

The electrical contact or coding means of the air-treatment device makes the variant of the air-treatment device advantageously identifiable and capable of being passed on to the controller in such a manner that this controller can operate the air-treatment device in accordance with the operating parameters prescribed for this air-treatment device. The controller may of course then be designed as a universal controller.

The electrical contact or coding means of the air-treatment device may be designed as a passive electrical component, e.g. as a resistor, capacitor or coil, or as an electronic circuit, e.g. as an ID chip or EEPROM.

A fixed resistor with a discrete resistance value has proved to be a particularly simple embodiment of the coding or contact means of the air-treatment device, wherein the discrete resistance value characterizes the operating voltage of the air-treatment device and can be evaluated by analog or digital means, e.g. by a microcomputer.

The air-treatment device may be designed as an ionizer, ozonator and/or electrical heater.

BRIEF DESCRIPTION OF THE DRAWING

The invention is explained in greater detail below with the help of an embodiment with reference to the drawing.

In the drawing.

SPECIFIC DESCRIPTION OF THE INVENTION

Figure 1:
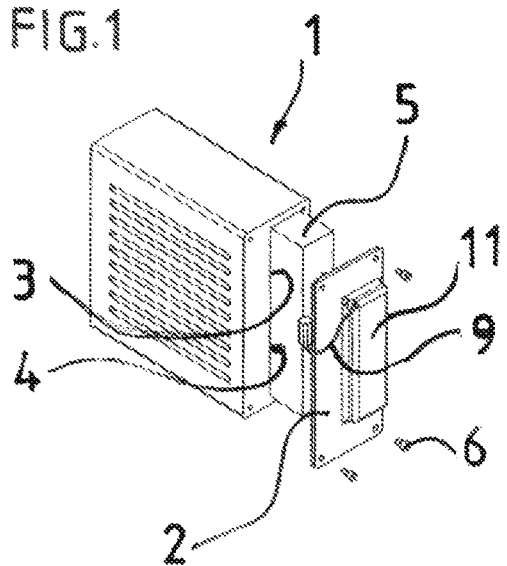
FIG. 1 is a perspective view for the present invention of the main parts of a vehicle air conditioner which include a service cover configured according to the invention and an air-treatment device configured according to the invention.
Figure 2:
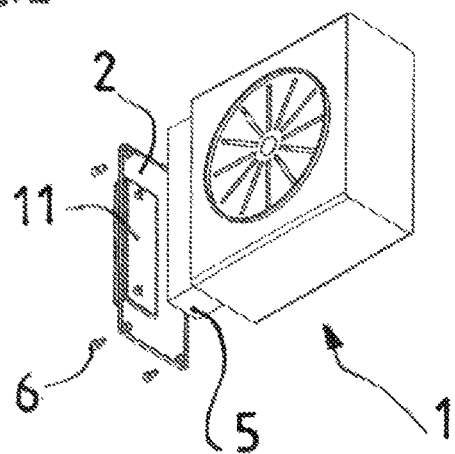
FIG. 2 is a perspective view corresponding to Figure is 1 from a rearward and opposite direction.

A vehicle air conditioner 1 shown in FIGS. 1 and 2 with the help of two perspective representations, in terms of the parts essential to the present invention, is normally used for the ventilation and air-conditioning of motor vehicle interiors.

Figure 3:
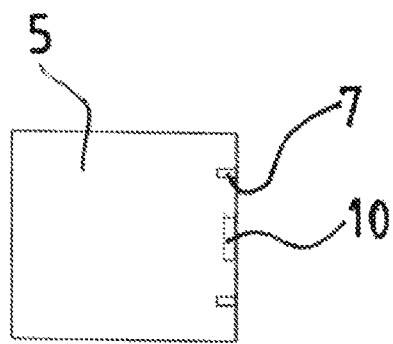
FIG. 3 is a schematic diagram of an air-treatment device of an air-treatment device according to the invention.
Figure 4:
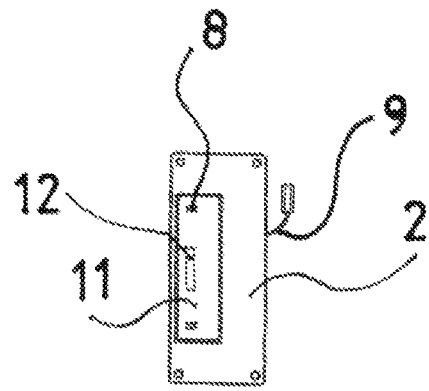
FIG. 4 is a schematic diagram of an embodiment of a service cover according to the invention.

A vehicle air conditioner 1 of this kind normally includes a service cover 2 a filter slot 3 of the vehicle air conditioner 1 can be closed, which has a service port 4. An air-treatment device 5 shown in FIGS. 1, 2 and 3 can be inserted through the service port 4 into the filter slot 3 of the vehicle air conditioner 1. Furthermore, this air-treatment device 5, which is an electric filter in the case of the embodiment of the vehicle air conditioner 1 shown in the figures, is exchangeable. Accordingly, a used electric filter 5 can thereby be easily exchanged and replaced with a fresh electric filter 5.

For this purpose, the service cover 2 which can be fastened to the vehicle air conditioner 1 by screws 6 is detached from this vehicle air conditioner 1. The air-treatment device or the electric filter can then be removed from the filter slot 3 of the vehicle air conditioner and exchanged for a fresh electric filter 5.

The electric filter 5 can be supplied with electrical energy by electrical means 7 provided on it using corresponding electrical means 8 provided on the service cover 2. For this purpose, the electrical means 8 of the service cover 2 are connected by an electrical connection line 9 to an electrical energy source.

The electric filter 5 includes, by way of example, an ionizer which can be supplied with electrical energy by the electrical means 7 on the electric filter side and the electrical means 8 on the service cover side via the electrical connection line 9. The electrical energy source not shown in the figures is usually arranged outside the actual vehicle air conditioner 1. In the case of the vehicle air conditioner 1 described above, the supply to the air treatment unit or the electric filter 5 takes place by the electrical means 7, 8 through the service cover 2.

In the exemplary embodiment represented, a contact means 10 is included in the air-treatment device 5 and the electric filter 5. The contact means 10 of the air-treatment device 5 comprises passive electrical components such as resistors, coils, capacitors, etc., for example, or electronic circuits, e.g. EEPROMs, ID chips, etc. These passive electrical components or electronic circuits are used as coding means for the model or type of the associated air-treatment device 5.

The service cover 2 that, as emerges in particular from FIGS. 1 and 2, closes the filter slot 3 in which the air-treatment device 5 is located has a controller 11 in the exemplary embodiment shown which is a universal controller. The controller 11 configured as a universally useable controller has a contact means 12 which makes a connection with the contact means 10 on the air-treatment part side when the service cover 2 is closed. The contact means 10 on the air-treatment device side that specifies the model or type of the air-treatment device 5 is read out or detected by the contact means 12 assigned to the controller 11 of the service cover 12. The controller 11 on the service cover side may operate the air-treatment device 5 accordingly, in line with a control program specified for the model or make of the same.

Since the variant or model of the respective air-treatment device 5 is adapted to the requirement profile set by the vehicle air conditioner 1, the controller 11 on the service cover side is capable of controlling or regulating the air-treatment device 5 accordingly.

The controller 11 integrated in the service cover 2 may be suitable in a corresponding way for a large number and variants of air-treatment devices 5. Accordingly, the development cost of a controller 11 of this kind, in which a wide variety of requirements such as reliability, EMC, functional testing, etc. have to be taken into account, can be reduced significantly, as a correspondingly adapted controller 11 does not need to be developed for each variant of an air-treatment device 5 or a vehicle air conditioner 1.

The interaction between the controller 11 and the contact means 10 of the air-treatment device 5 makes it possible for different variants of air-treatment devices 5 to be capable of being operated using the controller 11 designed as a universal controller.

The line connection between the contact means 10 of the air-treatment device 5, on the one hand, and the controller 11 on the service cover side, on the other, can be achieved by spring contacts, hard wiring, rubbing contacts, connectors, etc. If the contact means 10 on the air-treatment device side is designed as an electrical resistor in a structurally particularly simple embodiment, the resistance value of this electrical resistor can be specific to those variants of the air-treatment device 5 in which the electrical contact means 10 is installed.

When the air-treatment device 5 is embodied as an ionizer, the essential parameter for operation of the same is the electrical operating voltage. An electrical operating voltage of this kind can be very easily and universally coded by an electrical resistor. For example, discrete resistance values can stand for different operating voltages, e.g. 1 kOhm for 1000 Volt, 2 kOhm for 2000 Volt and 12 kOhm for 12000 Volt.

The corresponding resistance value of the electrical contact means 10 of the air-treatment device 5 is retrieved and detected by the controller 11 on the service cover side, after which the controller 11 on the service cover side controls or regulates the air-treatment device 5 in accordance with the detected resistance value of the electrical contact means 10.

The electrical contact means 10 of the air-treatment device 5 can effect robust personal protection with comparatively little expense, since data retrieval from the electrical contact means 10 of the air-treatment device 5 by the controller 11 on the service cover side can also be used for fault detection. If the value detected in the controller 11 on the service cover side for the electrical contact means 10 of the air-treatment device lies outside a permitted value range, or if a valid value cannot be detected at all, there is a fault or malfunction. One reason for a malfunction of this kind may, for example, be that the air-treatment device 5 is not mounted, or is not mounted correctly. This may be due to a temporary service event, for example, during which the air-treatment device 5 has been replaced cleaned or maintained. During this kind of service event, the ignition of the motor vehicle in whose air conditioner 1 the air-treatment device 5 is installed should be switched off. However, this is not guaranteed in all cases.

The controller 11 on the service cover side data is retrieved from the electrical contact means 10 of the air-treatment device 5, does not recognize a valid coding value of the electrical contact means 10 in a case like this. For safety reasons, or in order to achieve shock hazard protection, the operating voltage of the air-treatment device 5 is then limited to a value that does not represent a danger to life or the operating voltage of the air-treatment device 5 as a whole is switched off.

In the case of a controller 11 on the service cover side, without data retrieval from a valid electrical contact means, the controller 11 could switch the operating voltage of the air-treatment device 5 to 12000 V, for example, when the motor vehicle ignition is switched on without a plausibility check. It would not therefore be impossible for the staff carrying out the service work to come into contact with this high voltage.

With vehicle air conditioners 1 of this kind, the controller 11 on the service cover side operating voltage supplied from the motor vehicle can be changed into an operating voltage suitable for the air treatment unit 5. Consequently, for an air-treatment device configured as an ionizer, for example, a high voltage in the range of between 1 kV and 16 kV must be produced from a voltage of approx. 14 V supplied by the motor vehicle.

I claim:

1. In combination with a vehicle air conditioner having a filter slot with a service port and adapted to hold an electrical air-treatment device,
   a service cover having electrical means for electrically powering the air-treatment device in the slot to operate the air-treatment device from outside the vehicle air conditioner, and
   contact means on the service cover for coupling to a contact or coding means of the air-treatment device.

2. The combination according to claim 1, further comprising:
   an electrical controller on the service cover, providing an operating voltage for powering the air-treatment device, and contactable with the contact or coding means of the air-treatment device.

3. The combination according to claim 2, wherein an operating voltage of the electrical controller produced by the controller is at a level that does not represent a danger to life or is automatically switched off when the service port of the filter slot of the vehicle air conditioner is open or when the electrical connection between the electrical controller, on the one hand, and the contact or coding means of the air-treatment device, on the other, is interrupted.

4. A retrofit set for a vehicle air conditioner according to claim 2, wherein the set comprises the air-treatment device and the service cover.

5. The retrofit set according to claim 4, wherein the electrical contact or coding means identifying the variant of the air-treatment device is electrically couplable with the controller during assembly of the air-treatment device and the service cover and, after the electrical connection to the controller has been made, data can be retrieved therefrom.

6. The retrofit set according to claim 5, wherein the electrical contact or coding means identifies the variant of the air-treatment device to the controller in such a manner that the controller controls the air-treatment device in accordance with the operating parameters prescribed for the air-treatment device.

7. The retrofit set according to claim 4, wherein the electrical contact or coding means is a passive electrical resistor, capacitor, coil, an ID chip, or an EEPROM.

8. The retrofit set according to claim 7, the electrical contact or coding means is a fixed resistor with a discrete resistance value that characterizes the operating voltage of the air-treatment device and is evaluatable by analog or digital by a microcomputer.

9. The retrofit set according to claim 4, wherein the air-treatment device is an ionizer, ozonator, or electrical heater.

\* \* \* \* \*